United States Patent [19]

Mallion

[11] 4,233,454
[45] Nov. 11, 1980

[54] CYCLOPENTANE ACETIC ACID DERIVATIVES

[75] Inventor: Keith B. Mallion, Macclesfield, England

[73] Assignee: Imperial Chemical Industries Limited, London, England

[21] Appl. No.: 73,876

[22] Filed: Sep. 10, 1979

Related U.S. Application Data

[63] Continuation of Ser. No. 844,388, Oct. 21, 1977, abandoned.

[30] Foreign Application Priority Data

Nov. 16, 1976 [GB] United Kingdom ............... 47663/76
Dec. 8, 1976 [GB] United Kingdom ............... 51195/76

[51] Int. Cl.$^3$ ................. C07C 69/738; C07C 69/708; C07C 59/80; C07D 213/64
[52] U.S. Cl. ............................. 560/122; 260/343.3 P; 260/343.41; 542/426; 560/53; 562/463; 562/504
[58] Field of Search ................. 542/426; 560/53, 122; 562/463, 504

[56] References Cited

U.S. PATENT DOCUMENTS

| | | | |
|---|---|---|---|
| 3,652,643 | 3/1972 | Leir | 560/122 |
| 3,888,905 | 6/1975 | Miyano | 424/308 X |
| 3,910,965 | 10/1975 | Sakai et al. | 560/122 |
| 3,912,725 | 10/1975 | Leeming et al. | 542/426 |
| 3,952,019 | 4/1976 | Peel et al. | 260/343.2 R |
| 3,957,795 | 5/1976 | Kubela et al. | 560/122 |
| 4,020,172 | 4/1977 | Peel et al. | 260/343.2 R |
| 4,021,425 | 5/1977 | Mallion | 542/426 |

FOREIGN PATENT DOCUMENTS 1427541  3/1976  United Kingdom.

OTHER PUBLICATIONS

Peel, R., et al., *J. Chem. Soc., Chem. Comm*, 1974, pp. 151–153.
Corey, E., et al., *J. Am. Chem. Soc.*, 95, pp. 7522–7523 (1973).

*Primary Examiner*—Henry R. Jiles
*Assistant Examiner*—Richard A. Schwartz
*Attorney, Agent, or Firm*—Cushman, Darby & Cushman

[57] ABSTRACT

The disclosure relates to a novel sequence of reactions for manufacturing known prostaglandin intermediates, and to novel chemical intermediates obtained in the course of the novel reaction sequence, for example methyl 5$\beta$-chloro-2$\beta$-dimethoxymethyl-3$\alpha$-hydroxycyclopent-1$\alpha$-ylacetate.

3 Claims, No Drawings

CYCLOPENTANE ACETIC ACID DERIVATIVES

This is a continuation of application Ser. No. 844,388 filed Oct. 21, 1977, now abandoned.

This invention relates to a new chemical process for the manufacture of a known prostaglandin intermediate.

According to the invention there is provided a process for the manufacture of a known prostaglandin intermediate of the formula:

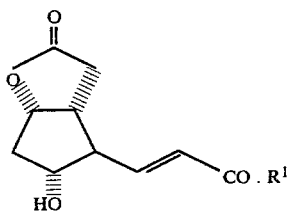
I wherein $R^1$ is a 4–7C alkyl radical, a phenoxymethyl radical optionally substituted in the phenyl part by a halogen atom, or a trifluoromethyl radical, or a pyridyloxymethyl radical optionally substituted in the pyridyl part by a halogen atom, from an aldehyde of the formula:

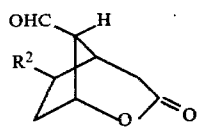
II wherein $R^2$ is a halogen atom, which comprises successively reacting:

(a)

(i) an aldehyde of the formula II with a 1–4C alkanol in the presence of a strong acid, (ii) the product so obtained, of the formula:

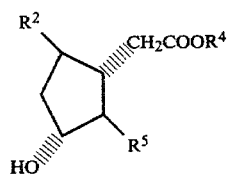
III wherein $R^2$ has the meaning stated above, $R^4$ is a 1–4C alkyl radical, and $R^5$ is a di(1–4C alkoxy)methyl radical, with an excess of an inorganic base, (iii) the product so obtained with a mineral acid, to give a reaction mixture of at least 0.5 N, (iv) the product so obtained with a phosphonate of the formula $(R^3O)_2PO.CH_2CO.R^1$, wherein $R^1$ has the meaning stated above and $R^3$ is a 1–4C alkyl radical, at a pH of about 8.5 to 9.0; or (b)

(i) an aldehyde of the formula II with a solution of a strong acid in a mixture of water and a water-miscible organic solvent, (ii) the product so obtained, of the formula III wherein $R^2$ has the meaning stated above, $R^4$ is a hydrogen atom and $R^5$ is a formyl radical, with a phosphonate of the formula $(R^3O)_2PO.CH_2COR^1$ wherein $R^1$ and $R^3$ have the meanings stated above, at a pH of about 8.5 to 9.0; or (c)

(i) an aldehyde of the formula II with a phosphonate of the formula $(R^3O)_2PO.CH_2CO.R^1$, wherein $R^1$ and $R^3$ have the meanings stated above, at a pH of about 8.5 to 9.0, (ii) the product so obtained with a solution of a strong acid in a mixture of water and a water-miscible organic solvent, (iii) the product so obtained, of the formula III wherein $R^2$ has the meaning stated above, $R^4$ is a hydrogen atom and $R^5$ is a radical of the formula:

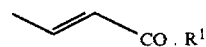
IV wherein $R^1$ has the meaning stated above, with a solution of an inorganic base in a mixture of water and a water-miscible organic solvent, to give a pH of about 8 to 9.

Suitable values for $R^1$ are, for example, n-pentyl, n-heptyl, 3-chlorophenoxymethyl, 3-trifluoromethylphenoxymethyl and 5-chloropyrid-2-yl radicals.

A suitable value for $R^2$ is, for example, a chlorine or bromine atom. A preferred value for $R^3$ in the above process is a methyl radical.

In process (a), a suitable alkanol is, for example, methanol or ethanol, and a suitable strong acid is, for example, toluene-p-sulphonic acid; a suitable inorganic base is, for example, sodium hydroxide or potassium hydroxide; and a suitable mineral acid is, for example, hydrochloric or sulphuric acid.

In process (b), a suitable strong acid is, for example, toluene-p-sulphonic acid, hydrochloric acid or sulphuric acid, and a suitable water-miscible organic solvent is, for example, acetone, dioxan or tetrahydrofuran.

In process (c), a suitable strong acid is, for example, hydrochloric acid, sulphuric acid, or toluene-p-sulphonic acid, a suitable water-miscible organic solvent is, for example, acetone, dioxan or tetrahydrofuran, and a suitable inorganic base is, for example, sodium or potassium carbonate, or sodium or potassium hydroxide.

In the reaction with a phosphonate of the formula $(R^3O)_2PO.CH_2CO.R^1$, a suitable pH is about 8.5–9.0 and is conveniently provided by the addition of an inorganic base, for example potassium carbonate, sodium carbonate, sodium hydroxide or potassium hydroxide.

All the stages in the above process are conveniently carried out at a temperature no higher than ambient room temperature, and any stage which involves changing the pH of the reaction medium from acidic to basic, or vice versa, may if desired be carried out using water- or ice-cooling.

It is convenient to carry out the above process in a streamlined or telescoped manner, without isolating the intermediate products after each state, as losses of yield in the isolation procedures are thereby avoided, but any one or more of the intermediate products may of course be isolated, and optionally purified, if desired.

The intermediate products of the formula III which are formed in the process of the invention are novel compounds, and form a further feature of this invention.

Thus, according to a further feature of the invention there is provided a cyclopentane derivative of the formula III wherein $R^2$ has the meaning stated above, $R^4$ is a hydrogen atom or a 1–4C alkyl radical, for example a methyl or ethyl radical, and $R^5$ is a di(1–4C alkoxy)-methyl or formyl radical, or a radical of the formula IV.

Particular cyclopentane derivatives of the invention of the formula III are methyl 5β-chloro-2β-dimethoxymethyl-3α-hydroxycyclopent-1α-ylacetate, 5β-chloro-2β-formyl-3α-hydroxycyclopent-1α-ylacetic acid and 5β-chloro-2β-[4-(3-chlorophenoxy)-3-oxobut-1-trans-enyl]-3α-hydroxycyclopent-1α-ylacetic acid.

The invention is illustrated but not limited by the following Examples:

EXAMPLE 1

6-exo-Chloro-3-oxo-2-oxabicyclo[3,2,1]octane-8-anticarbaldehyde*, (prepared as described below), was dissolved in methanol (5 ml.) and toluene-p-sulphonic acid (0.65 g.) was added. After 3 hours, a solution of sodium hydroxide (1.08 g.) in water (15 ml.), was added to the reaction mixture, which was then stirred for ½ hour at room temperature. The reaction mixture was washed with ethyl acetate (2×15 ml.), the combined toluene washes were back-extracted with water (4 ml.) and the aqueous extract was combined with the aqueous reaction mixture, which was neutralised with 5 N-hydrochloric acid and then made to 0.5 N by the addition of 6 N-hydrochloric acid (2.2 ml.). This solution was stirred overnight at room temperature, then cooled to 0°–5° C. and neutralised with solid potassium carbonate. A solution of dimethyl [3-(3-chlorophenoxy)-2-oxopropyl]phosphonate (1.96 g.) in tetrahydrofuran (12 ml.) was then added, followed by the addition of a solution of anhydrous potassium carbonate (2.3 g.) in water (12 ml.) over 1 hour. The mixture was stirred for 20 minutes, then glyoxylic acid monohydrate (1.0 g.) was added, and the mixture was stirred for a further 1 hour. The reaction mixture was extracted with toluene (30 ml.), then with a mixture of ethyl acetate (10 ml.) and toluene (20 ml.). The combined organic extracts were washed with water (5 ml.) and saturated brine (15 ml.) and dried, and the solvents were evaporated to give a gum which solidified after being left stirring overnight under toluene to give 4β-[4-(3-chlorophenoxy)-3-oxobut-1-trans-enyl]-2,3,3aβ,6aβ-tetrahydro-5α-hydroxy-2-oxocyclopenteno[b]furan, identical by thin layer chromatography and infra-red and n.m.r. spectroscopy with an authentic sample, m.p. 103°–104° C.

*anti refers to the substituent lying on the opposite side of the C-8 bridge of the 2-oxa atom.

The 6-exo-chloro-3-oxo-2-oxabicyclo[3,2,1]octane-8-anti-carbaldehyde used as starting material may be obtained as follows:

6-exo-Chloro-3-oxo-2-oxabicyclo[3,2,1]octane-8-anti-carboxylic acid (1.38 g.) was suspended in dry toluene (5.5 ml. analytical quality) and dry dimethylformamide (0.035 ml.) under an atmosphere of argon. Thionyl chloride (1.94 ml.) was added, and the mixture was stirred, and heated to 50° C. for 80 minutes (a clear solution was normally obtained in about 45–60 minutes). The solution was cooled to room temperature, and the solvents were evaporated to give a gum which crystallised. The gum was dried by azeotropic distillation of toluene therefrom, and then in a vacuum desiccator under high vacuum, to give 6-exo-chloro-3-oxo-2-oxabicyclo[3,2,-1]octane-8-anti-carbonyl chloride.

A mixture of 10% w/w palladium-on-charcoal (0.3 g.) in acetone (30 ml., analytical quality) and N,N-dimethylaniline (1.0 ml.) was stirred under an atmosphere of hydrogen for 1¼ hours. A solution of 6-exo-chloro-3-oxo-2-oxabicyclo[3,2,1]octane-8-anti-carbonyl chloride (1.49 g.) in acetone (10 ml., analytical quality) was added from a syringe through a serum cap, and the mixture was stirred for ¾ hour. The reaction mixture was filtered through kieselguhr ("Hyflo"—trade mark) and the filter cake was washed with analytical quality acetone. The filtrate was evaporated to dryness under reduced pressure at room temperature, to give 6-exo-chloro-3-oxo-2-oxabicyclo[3,2,1]octane-8-anti-carbaldehyde as a gum, $R_f$=0.5 (10% v/v methanol in chloroform), which was used without purification as the starting material for the above-described process.

EXAMPLE 2

To a solution of 6-exo-chloro-3-oxo-2-oxabicyclo[3,2,1]octane-8-anti-carbaldehyde in acetone containing N,N-dimethylaniline, (the filtrate and washings from the catalytic hydrogenation of the corresponding acid chloride, described in the latter part of Example 1) was added a solution of toluene-p-sulphonic acid (1.2 g.) in water (5 ml.) and the mixture was stored under an atmosphere of argon at room temperature for 4 days. To this reaction mixture, stirred at room temperature, was added dimethyl [3-(3-chlorophenoxy)-2-oxopropyl]phosphonate (2.75 g.), followed by a solution of potassium carbonate (2.67 g.) in water (10 ml.) dropwise over 50 minutes. Forty minutes after the addition was completed, glyoxylic acid monohydrate (1.14 g.) and anhydrous potassium carbonate (2.57 g.) were added. The mixture was stirred for 20 minutes, and then partitioned between ethyl acetate (90 ml.) and 2 N hydrochloric acid (60 ml.). The aqueous layer was separated and washed with ethyl acetate (90 ml.), and the combined ethyl acetate solutions were washed with 2 N hydrochloric acid (30 ml.), then with saturated sodium bicarbonate solution (2×20 ml.) and finally with brine (20 ml.). The organic solution was dried, decolorised with carbon ("Actibon S"—trade mark) and filtered, and the solvent was evaporated to give a crude gum. The gum was triturated with toluene to give crystalline 4β-[4-(3-chlorophenoxy)-3-oxobut-1-trans-enyl]-2,3,3aβ,6aβ-tetrahydro-5α-hydroxy-2-oxocyclopenteno[b]furan, identical by thin-layer chromatography with an authentic sample, m.p. 103°–104° C.

EXAMPLE 3

A solution of 6-exo-chloro-3-oxo-2-oxabicyclo[3,2,-1]octane-8-anti-aldehyde in acetone containing N,N-dimethylaniline, (the filtrate and washings from the catalytic hydrogenation of the corresponding acid chloride, described in the latter part of Example 1), was diluted with water (3 ml.), then dimethyl [3-(3-chlorophenoxy)-2-oxopropyl]phosphonate (2.74 g.) was added, followed by a solution of potassium carbonate (1.3 g.) in water (10 ml.) dropwise over 15 minutes. The reaction mixture was adjusted to pH 4 by the addition of 1:1 v/v concentrated hydrochloric acid:water, toluene-p-sulphonic acid (1.02 g.) was added, and the reaction mixture was kept at room temperature for 4 days under an atmosphere of argon. The pH was adjusted to about 8–9 by adding concentrated aqueous potassium carbonate dropwise, then glyoxylic acid monohydrate (1.3 g.) and potassium carbonate (4.0 g.) were added, and the mixture was stirred at room temperature for 20 minutes, then neutralised with 2 N hydrochloric acid. The acetone was evaporated under reduced pressure, and the aqueous solution was extracted with ethyl acetate (2×90 ml.). The combined extracts were washed with 2 N hydrochloric acid, then with sodium bicarbonate solution and finally with brine, and were then dried. The solvents were evaporated under reduced pressure, and the residual gum crystallised on trituration with ethyl acetate/ether, giving 4β-[4-(3-chlorophenoxy)-3-oxobut-1-trans-enyl]-2,3,3aβ,6aβ-tetrahydro-5α-hydroxy-2-oxocyclopenteno[b]furan, identical by thin layer chromatography with an authentic sample, m.p. 103°–104° C.

EXAMPLE 4

A solution of 6-exo-chloro-3-oxo-2-oxabicyclo[3,2,1]octane-8-anti-carbaldehyde in analytical quality acetone, (containing 3% palladium-on-charcoal and N,N-dimethylaniline used in its preparation from the corresponding acid chloride, as described below), was stirred under an atmosphere of argon, and a solution of toluene-p-sulphonic acid (3.12 g.) in dry methanol (15 ml.) was added rapidly. The mixture was stirred overnight, then cooled in a cold water-bath while a solution of sodium hydroxide (5.25 g.) in water (36 ml.) was added, and after a further 1 hour of stirring, 6 N hydrochloric acid (30 ml.) was added over 5 minutes. The mixture was stirred for a further 2 hours, and filtered to remove the palladium catalyst, which was washed with acetone (5 ml.) then water (9 ml.). After a further 1 hour, the clear filtrate was cooled to about 5° C. in an ice-bath, and stirred vigorously while being neutralised by the addition of solid potassium carbonate (8.11 g.).

Solid dimethyl [3-(3-chlorophenoxy)-2-oxopropyl]-phosphonate (5.88 g.) was then added to the neutralised filtrate, followed by acetone (15 ml.) to assist its dissolution. The ice-bath was removed, and a solution of potassium carbonate (6.9 g.) in water (36 ml.) was added at 15°–20° C. over 50 minutes. Half an hour after completion of this addition, solid glyoxylic acid monohydrate (3.0 g.) was added, the mixture was stirred for a further ½ hour, and was then extracted with toluene (75 ml.) followed by two 75 ml. portions of a 2:3 v/v mixture of ethyl acetate and toluene. The organic extracts were combined, washed successively with saturated aqueous sodium bicarbonate solution (45 ml.), 2 N hydrochloric acid (90 ml. then 30 ml.) and brine (30 ml.), dried over magnesium sulphate, and decolourised with charcoal. The solvents were evaporated, and the gummy residue crystallised on stirring with toluene to give 4β-[4-(3-chlorophenoxy)-3-oxobut-1-trans-enyl]-2,3,3aβ,6,6aβ-tetrahydro-5α-hydroxy-2-oxocyclopenteno[b]furan, identical with the product described in Example 1.

The solution of 6-exo-chloro-3-oxo-2-oxabicyclo[3,2,1]octane-8-anti-carbaldehyde, used as the starting material in the above process, was obtained as follows:

6-exo-Chloro-3-oxo-2-oxabicyclo[3,2,1]octane-8-anticarboxylic acid (4.128 g.) was suspended in dry toluene (16.5 ml.) and stirred under an atmosphere of argon, thionyl chloride (2.184 ml.) was added, followed by dimethylformamide (0.105 ml.), and the mixture was stirred at 50° C. for about 3 hours, until a clear solution was obtained. After a further 15 minutes, the solution was cooled to room temperature, excess sulphur dioxide and hydrogen chloride were removed by briefly evacuating the reaction vessel and crystalline acid chloride, 6-exo-chloro-3-oxo-2-oxabicyclo[3,2,1]octane-8-anti-carbonyl chloride, was precipitated by the addition of hexane (15 ml. added slowly, and then 18 ml. added rapidly). The crystalline acid chloride was separated by filtration, and washed on the filter with hexane (2×18 ml. and 1×9 ml.), at all times ensuring that the acid chloride on the filter was covered by solvent to avoid direct exposure to the atmosphere. After this washing process, the acid chloride was dissolved through the filter into a clean receiver with analytical quality acetone (33 ml.).

A mixture of 3% w/w palladium-on-charcoal (1.5 g.), N,N-dimethylaniline (3 ml.) and analytical quality acetone (15 ml.) was stirred in an atmosphere of hydrogen at slightly above atmospheric pressure for 1 hour, then the acetone solution of the acid chloride described above was added rapidly. The reduction of the acid chloride was monitored by thin layer chromatography on silica gel, eluting with 10% v/v methanol in chloroform, and reduction was usually complete in 2 to 3 hours. The hydrogen atmosphere was replaced by argon, and the total mixture was then used as the starting material in the process described above.

What we claim is:

1. A cyclopentane derivative of the formula:

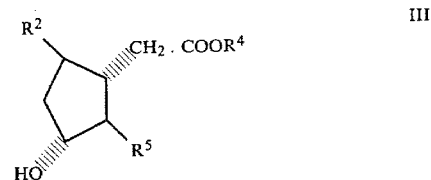

wherein $R^2$ is halogen, $R^4$ is hydrogen or 1–4C alkyl and $R^5$ is di(1–4C or a radical of the formula:

wherein $R^1$ is 4–7C alkyl, phenoxymethyl or phenoxymethyl substituted in the phenyl part by halogen or trifluoromethyl, or 2-pyridyloxymethyl or 2-pyridyloxymethyl substituted in the pyridyl part by halogen.

2. Methyl 5β-chloro-2β-dimethoxymethyl-3α-hydroxycyclopent-1α-ylacetate.

3. 5β-Chloro-2β-[4-(3-chlorophenoxy)-3-oxobut-1-trans-enyl]-3α-hydroxycyclopent-1α-ylacetic acid.

* * * * *